United States Patent [19]

Vanhumbeeck et al.

[11] Patent Number: 4,545,957
[45] Date of Patent: Oct. 8, 1985

[54] ANALYSIS SYSTEM FOR DETERMINING COPPER CONTENT IN WASTE WATER

[75] Inventors: Jacky Vanhumbeeck, Brugge; Laurent Danneels, Varsenare; Hubert De Steur, Drongen; Guido Heyneman, Knokke, all of Belgium

[73] Assignee: Siemens Aktiengesellschaft, Berlin & Munich, Fed. Rep. of Germany

[21] Appl. No.: 345,924

[22] Filed: Feb. 4, 1982

[30] Foreign Application Priority Data

Mar. 30, 1981 [DE] Fed. Rep. of Germany ....... 3112553

[51] Int. Cl.⁴ .............................................. G01N 21/25
[52] U.S. Cl. ....................................................... 422/81
[58] Field of Search ............... 422/81, 68, 67; 436/43, 436/80, 164

[56] References Cited

U.S. PATENT DOCUMENTS

| | | | |
|---|---|---|---|
| 2,950,396 | 8/1960 | Schneider | 422/81 |
| 3,030,192 | 4/1962 | Schneider | 422/81 |
| 3,227,523 | 1/1966 | Hoefker et al. | 422/81 |
| 4,326,940 | 4/1982 | Eckles et al. | 422/81 |
| 4,391,775 | 7/1983 | Huber et al. | 422/81 |

Primary Examiner—Hiram H. Bernstein
Attorney, Agent, or Firm—Hill, Van Santen, Steadman & Simpson

[57] ABSTRACT

An analysis system for determining total copper content in waste-water, as from a galvanizing system, comprises periodically taking samples from such waste-water, acidifying such samples with a metalliferous acid containing a metal which forms a strong cyanogen complex and which exhibits a larger electro-negative potential than copper, such as Pd, reducing cupric ions to cuprous ions, adjusting the pH of the resulting sample solution, adding a copper color-forming reagent, such as bathocuprione disulfonic acid salt, and determining the color content by colorimetry. In order to determine a reagent value, a prepared waste-water sample can be subjected to colorimetry before and after addition of the color-forming reagent.

1 Claim, 1 Drawing Figure

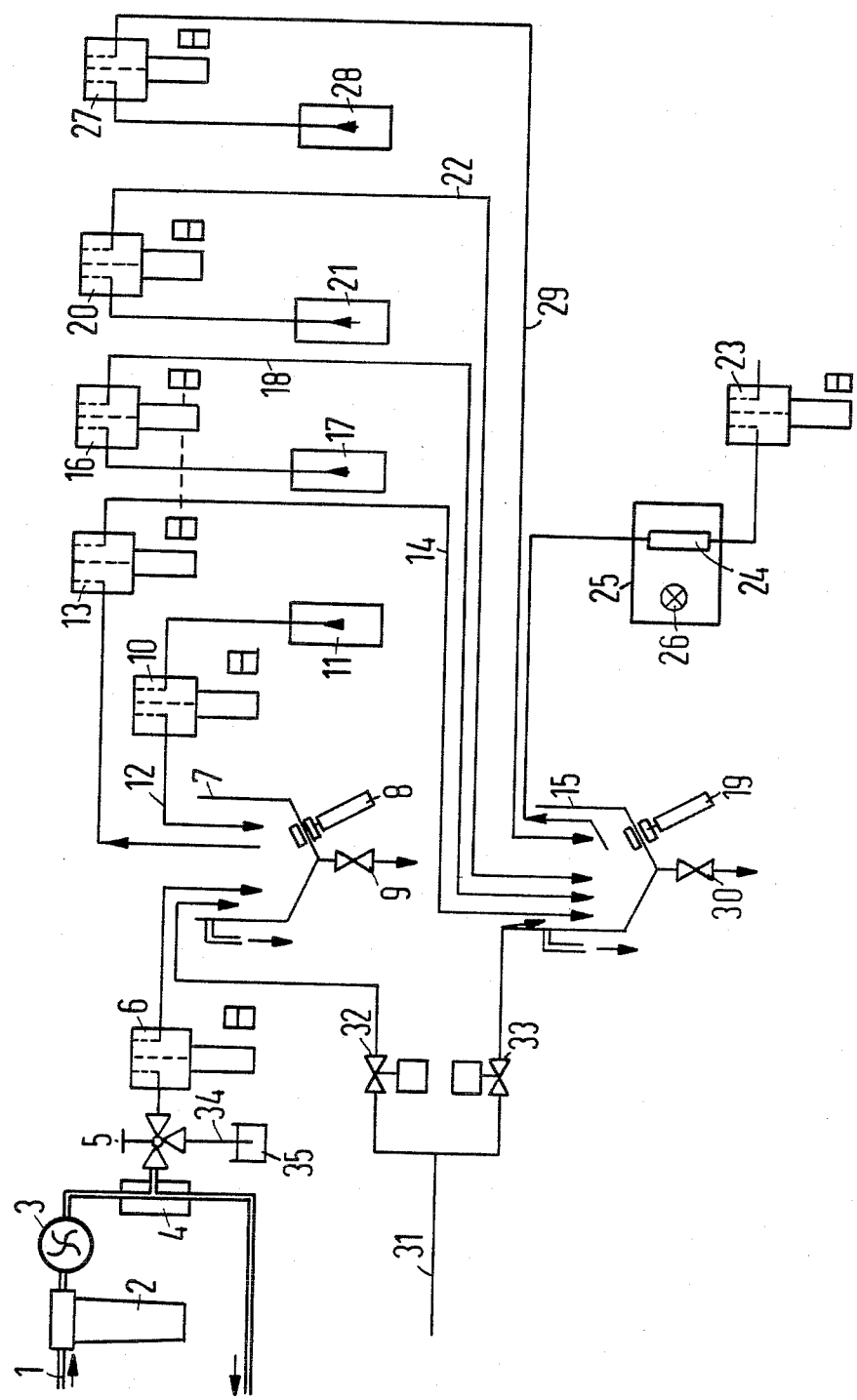

ANALYSIS SYSTEM FOR DETERMINING COPPER CONTENT IN WASTE WATER

BACKGROUND OF THE INVENTION

1. Field of the Invention

The invention relates to an analysis system and device for determining copper in waste water and somewhat more particularly to a system and device for determining free and complexed copper in waste water of a galvanizing system.

2. Prior Art

Analysis systems for determining copper content in waste water, as in waste water of galvanizing systems, are known wherein waste water samples are taken from the waste water, preferably at pre-selected intervals, and collected in a suitable container, any bivalent copper in such samples is reduced to monovalent copper by addition of a reduction agent and, after attaining a specific pH-value with a buffer solution, a copper color-forming reagent is added and the copper content in the prepared sample is determined by colorimetry.

These types of analysis systems function to continuously automatically measure copper content in waste water. However, with such systems, only free copper contained in the waste water can be determined, but not copper bonded to cyanogen, such as particularly occurs in waste-water of galvanizing systems.

SUMMARY OF THE INVENTION

The invention provides an analysis system and device of the above described type, but which allows the total (free and bonded) copper content in a waste water to be determined and, if desired, recorded.

In accordance with the principles of the invention, analysis systems and devices of the type above described are improved in a relatively simple manner by acidifying waste water samples directly after sample taking with a metal-containing acid having a metal which forms cyanogen complexes and which exhibits a larger electro-negative potential than copper so that it forms a stronger cyanogen complex than the copper cyanogen complex present in the waste water.

By acidifying a waste water sample with a metalliferous acid, any bonded copper and any copper which, under certain conditions, may exist as a hydroxide, is converted into ionogenic form. Primarily, any copper cyanogen complex is destroyed by acidification with a metalliferous acid. In preferred embodiments of the invention, the metalliferous acid is a palladium-containing hydrochloric acid, which when added to waste water containing a copper cyanogen complex, destroys such complex with the palladium and forms an extremely stable $Pd(CN)_4^{-2}$ complex.

In certain embodiments of the invention, sample preparation occurs in a separate container from an analysis container and waste water samples are taken from the waste water undergoing analysis at specific time intervals while the analysis is being conducted. The use of two containers is advantageous in that sample taking can occur during analysis so as to allow an integration of the amount of a harmful substance in the waste water.

In certain embodiments of the invention, in order to eliminate false readings due to self-coloration and turbidity of a waste water sample, the intensity, A, of transmitted light in a colorimeter before the addition of a color-forming reagent and the intensity, B, of transmitted light after such addition is measured and, with the assistance of a microprocessor, the absorption value, $k(\log A - \log B)$, is calculated, wherein k is a calibration factor.

BRIEF DESCRIPTION OF THE DRAWING

The FIGURE is a schematic illustration of an analysis system and device functioning in accordance with the principles of the invention.

DESCRIPTION OF THE PREFERRED EMBODIMENTS

A waste water to be analyzed or at least a portion of such waste water (typically known to contain an unknown amount of copper, both complexed and free) is fed through a closed circuit pipeline 1 to a sample-taking location 4 of an analysis system via a coarse filter 2 with the assistance of a circulatory pump 3. The waste-water flow direction is schematically indicated with arrows associated with the pipeline 1. As a function of a selected analysis interval, samples are periodically taken from this closed circuit via a three-way tap or valve means 5 with the assistance of a metering syringe 6 and are collected in a first or storage container 7. Selectable analysis intervals of 15, 30 or 60 minutes are recommended, although other intervals can also be used. Corresponding to a selected analysis interval, a waste-water sample can be taken every 2.5, 5 or 10 minutes. The storage container 7 can be equipped in a known manner with an electro-mechanical agitator 8 and a discharge valve 9. Waste-water samples are continuously taken at select intervals from the waste water being tested or analyzed and are fed to the storage container 7 wherein the agitator 8 insures that a thorough mixing occurs so as to obtain a substantially uniform collected sample. Corresponding to previously specified intervals, a copper analysis of the collected sample occurs every 15, 30 or 60 minutes. In an exemplary embodiment of the invention, for example, after five initial samples have been collected in container 7, a predetermined amount of a metalliferous acid is transferred from a reservoir 11 thereof with the aid of a metering syringe 10 into the storage container 7 via a fluid line 12. Again, the agitator 8 is activated for a limited time so as to obtain a uniform mixture.

In preferred embodiments of the invention, 4 ml of HCl 5 N $Pd^{+2}$ (1 g/l) is added as the metalliferous acid to the collected waste water sample so as to destroy any copper cyanogen complex present in such sample and form an extremely stable $Pd(CN)_4^{-2}$ complex. Any existing copper hydroxide in the waste-water sample is dissolved upon addition of the metalliferous acid.

With the assistance of a metering syringe 13 and an appropriate fluid line, 20 ml of the acidified waste-water sample are taken from container 7 and transferred into a second or analysis container 15 via a fluid line 14. Substantially, at the same time, 4 ml of a hydroxyl ammonium chloride solution are taken with the assistance of a further metering syringe 16 from a reservoir 17 thereof and are transferred to the analysis container 15 via a fluid line 18. In this manner, any bivalent copper present in the acidified waste-water sample is reduced to monovalent copper. The container 15 is also equipped with an electro-mechanical agitator 19, which is activated at appropriate times to ensure a thorough mixing of the various components present in container 15. A predetermined amount of sodium citrate is also taken from a reservoir 21 thereof with the aid of a metering syringe 20 and is transferred to container 15 via a line 22.

In the embodiment illustrated, a portion of the solution in container 15 is removed with the assistance of an interconnected metering syringe 23 and transferred into a measuring bulb 24 of a colorimeter 25, which can be of a known type. The colorimeter 25 preferrably includes an irradiation system, such as a light source 26. With the assistance of this colorimeter, the intensity, A, of transmitted light through the prepared sample in bulb 24 is measured at 475 nm, which corresponds to the actual reagent value of the solution and, if desired, recorded. The amount of prepared sample in bulb 24 is ejected therefrom back into the analysis container 15 with a reverse operation of syringe 23 and the agitator 19 is again activated to provide a uniform solution. Thereafter, 4 ml of a color-forming reagent for copper is removed from a reservoir 28 thereof with a further metering syringe 27 and transferred to container 15 via a fluid line 29. In an exemplary embodiment, bathocuproine disulfonic acid is utilized as such a color-forming reagent. In a pH range of 3.5 through 11, monovalent copper ions form a water-soluble, orange-colored complex with the disodium salt of bathocupronie disulfonic acid, and which exhibits an absorption maximum at 475 nm. Since some metal ions can interfere with copper determination, sodium citrate can be added for masking.

After a thorough mixing of the prepared sample solution with the color-forming reagent, a portion of the result of solution is again transferred to the measuring bulb 24 of colorimeter 25 with the assistance of metering syringe 23. While not absolute necessary, it is recommended that the bulb 24 be rinsed, as by at least once ejecting the just-fed solution back to container 15 and re-drawing the same. The intensity B, of transmitted light through bulb 24 is again measured at 475 nm and recorded, if desired. The measured signals of the light intensities, A and B are amplified in the colorimeter and are transmitted to a microprocessor (not shown) which calculates an absorption value, log A−log B. Multiplication of this value with a calibration factor, k, yields the copper concentration in the waste-water being analyzed.

After the measurement, the drawn-in amount of prepared sample in bulb 24 is again ejected into analysis container 15. When all measurements are completed, the contents of container 15 are discharged, for example, into the waste water, via discharge valve 30.

A suitable rinsing liquid can be provided from a reservoir thereof, (not shown) via a line 31 through valves 32 and 33 to the first and second containers 7 and 15, respectively, as well as to the measuring bulb 24.

The three-way tap 5 can be connected with a branch line 34 to a container 35, containing a suitable calibration solution or reagent value solution. In this manner, one can correspondingly calibrate the analysis system or device (zero point and slope of the calibration line).

The various metering syringes 6, 10, 13, 16, 20, 23 and 27 are all preferably pneumatically controlled. Appropriate details of such metering syringes are known, for example, from German No. DE OS 29 10 646.

Control of the above-described process sequence can occur with an electronic control means containing a microprocessor, so that a fully automatic control is readily attained.

The functional precision of the analysis device and/or system can be checked at any time with the aid of a calibration program.

As is apparent from the foregoing specification, the present invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, accepting as it is set forth and defined in the hetero-attended claims.

We claim as our invention:

1. An automatic analysis device for determining total copper content in a waste-water containing an unknown amount of copper, comprising:

a first container and a second container,
means for periodically taking aqueous samples from such waste-water and for transferring such samples to said first container to form a sample batch in said first container;
means for mixing said sample batch taken in said first container;
means for adding to, and acidifying said sample batch in said first container with, a predetermined amount of a predetermined liquid that incorporates a metalliferous acid containing a metal which forms a cyanogen complex and which exhibits a larger electronegative potential than copper;
means for transferring a predetermined portion of the resulting so acidified sample batch from said first container to said second container;
means for mixing said predetermined portion in said second container;
means for adding a predetermined amount of a predetermined reducing agent solution to said second container so as to reduce any bivalent copper present in said predetermined portion to monovalent copper;
means for adding a predetermined amount of a predetermined buffer solution to said second container so as to adjust the pH of said predetermined portion to a value in the range from about 3.5 through 11;
means for adding a predetermined amount of a predetermined color-forming reagent solution for copper to said second container;
a colorimetric measuring bulb means,
means for transferring a predetermined quantity of the resulting such predetermined portion from said second container into said colorimetric measuring bulb means;
means including a microprocessor for measuring an absorption value for the intensity of a transmitted light which is passed through said predetermined quantity in said measuring bulb means;
means for determining the self-coloration and turbidity of said so adjusted predetermined portion whereby the intensity, A, of light transmitted through a predetermined quantity of said so adjusted predetermined portion before the addition of said color-forming reagent is measured and the absorption value k (log A−log B) thereof is calculated with the aid of said microprocessor, wherein k is the calibration factor, and
means for sequencing and controlling the operation of said analysis device.

* * * * *